US010068318B2

(12) United States Patent
Dzyubak et al.

(10) Patent No.: US 10,068,318 B2
(45) Date of Patent: Sep. 4, 2018

(54) ENHANCING THE DETECTABILITY OF OBJECTS IN MEDICAL IMAGES

(71) Applicant: MAYO FOUNDATION FOR MEDICAL EDUCATION AND RESEARCH, Rochester, MN (US)

(72) Inventors: Bogdan Dzyubak, Rochester, MN (US); Richard L. Ehman, Rochester, MN (US); Armando Manduca, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 178 days.

(21) Appl. No.: 14/989,781

(22) Filed: Jan. 6, 2016

(65) Prior Publication Data

US 2016/0203589 A1     Jul. 14, 2016

Related U.S. Application Data

(60) Provisional application No. 62/100,296, filed on Jan. 6, 2015.

(51) Int. Cl.
*G06T 5/00* (2006.01)
*A61B 6/00* (2006.01)
*A61B 6/03* (2006.01)

(52) U.S. Cl.
CPC ............. *G06T 5/002* (2013.01); *A61B 6/486* (2013.01); *A61B 6/5258* (2013.01); *A61B 6/032* (2013.01); *A61B 6/037* (2013.01); *G06T 2207/10081* (2013.01); *G06T 2207/20012* (2013.01)

(58) Field of Classification Search
USPC .......................................... 382/128, 254, 274
See application file for complete search history.

(56) References Cited

U.S. PATENT DOCUMENTS

| 7,668,699 | B2* | 2/2010 | Chen ...................... H04B 17/26 |
| | | | 702/181 |
| 8,214,177 | B2* | 7/2012 | Peng ...................... A61B 6/502 |
| | | | 702/179 |
| 8,774,480 | B2  | 7/2014 | Roy et al. |
| 2011/0091130 | A1* | 4/2011 | Faubert ................ G09G 3/2048 |
| | | | 382/275 |
| 2011/0116699 | A1* | 5/2011 | Roy ........................ G06T 5/008 |
| | | | 382/131 |

OTHER PUBLICATIONS

Yeh, et al. Application of Stochastic Resonance for Imaging Enhancement of Computed Tomography in Hepatocellular Carcinoma, 2011 IEEE International Conference on Bioinformatics and Biomedicine Workshops, pp. 945-947.

(Continued)

*Primary Examiner* — Ishrat I Sherali
(74) *Attorney, Agent, or Firm* — Quarles & Brady LLP

(57) ABSTRACT

A system and method is provided for enhancing the detectability of objects in medical images. The method includes providing medical imaging data acquired using a medical imaging system, integrating dynamic noise with the imaging data to generate a modified set of images that achieves improved detection accuracy, and displaying the modified images.

18 Claims, 8 Drawing Sheets

(56) References Cited

OTHER PUBLICATIONS

Jha, et al. Noise-induced Contrast Enhancement of Dark Images using Non-dynamic Stochastic Resonance, 2012, IEEE, 5 pages.
Chouhan, et al. Wavelet-based contrast enhancement of dark images using dynamic stochastic resonance (Conference Paper), ACM International Conference Proceeding Series, 8th Indian Conference on Computer Vision, Graphics and Image Processing, 2012, Abstract Only, 1 page.

\* cited by examiner

ENHANCING THE DETECTABILITY OF OBJECTS IN MEDICAL IMAGES

CROSS-REFERENCE TO RELATED APPLICATIONS

This application is based on, claims priority to, and incorporates herein by reference in its entirety, U.S. Provisional Patent Application Ser. No. 62/100,296, filed Jan. 6, 2015, and entitled, "System And Method For Enhancement of Medical Images."

BACKGROUND

The present disclosure relates to systems and methods for medical imaging and, more particularly, to systems and methods for enhancing images acquired using any of a variety of imaging modalities.

The most common way of extracting information from medical images remains visual analysis by a radiologist, or another trained specialist, which is aimed at determining if an object (e.g. tumor) is present or grading a feature which spans a large portion of the image (e.g. classifying the lung tissue as being healthy or having emphysema). Objects in an image can be hard to detect if the image has a low contrast-to-noise ratio. Increasing object contrast is especially difficult in medical images as it can lead to increased radiation dose or significantly increased scan times. Thus, low contrast-to-noise ratios are especially common in medical imaging. Various methods have been used to enhance medical images, such as smoothing, edge enhancement, histogram equalization, and denoising algorithms. In general, most of these try to reduce noise in the image while maintaining desired features, or to increase contrast in the image.

SUMMARY

The present disclosure provides a system and method for enhancing the detectability of objects or features by a human observer in electronic medical images. This enhanced detectability can be achieved, counterintuitively, by adding dynamic noise to the images. Thus, the present disclosure describes a fundamentally different approach to increasing the detectability of objects in an image, based on adding a small amount of dynamic noise, to exploit a phenomenon termed "stochastic resonance."

In accordance with one aspect of the present disclosure, a method is provided for enhancing the detectability of objects in medical images. The method includes providing medical imaging data acquired using a medical imaging system and integrating dynamic noise with the imaging data to generate a series of images with varying noise, wherein each image in the series of images with varying noise includes dynamic noise. The method also includes analyzing the series of images with varying noise to determine dynamic noise parameters that achieve an improved detection accuracy and displaying images using the dynamic noise with noise parameters that achieves improved detection accuracy.

In accordance with another aspect of the present disclosure, a method is provided for enhancing the detectability of objects in medical images. The method includes providing medical imaging data acquired using a medical imaging system and generating multiple instances of a single medical image from the medical imaging data. the method also includes integrating dynamic noise signals with each of the multiple instances of the single medical image to generate a series of images with varying noise, wherein each of the multiple instances of the single medical image is integrated with a different dynamic noise signal to create a series of modified images and displaying, on a display, the series of modified images.

In accordance with yet another aspect of the present disclosure, a system is provided for enhancing medical images. The system includes a receiving unit that receives medical imaging data acquired using a medical imaging system and an image generating unit that generates multiple instances of a medical image from the medical imaging data. The system also includes a noise generating unit that generates noise signals, an image integrating unit that integrates the noise signals with each of the multiple instances of the single medical image to generate a series of images with varying noise, and an image displaying unit that displays the series of images with varying noise.

In accordance with still another aspect of the present disclosure a method is provided for enhancing the detectability of objects in medical images. The method includes providing medical imaging data acquired using a medical imaging system, integrating dynamic noise with the imaging data to generate a modified set of images that achieves improved detection accuracy, and displaying the modified images.

The foregoing and other advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

In medical imaging, noise is generally considered undesirable. Thus, a noisy image generally reduces the likelihood of accurate diagnosis (e.g. detection of a tumor or staging of disease based on anatomical changers or patterns). Thus, extensive efforts have been made for all medical imaging modalities to control, reduce, or overcome noise in the images, because noise is generally understood to obscure the underlying signal or information within the images that the clinician is considering.

Figure 9:
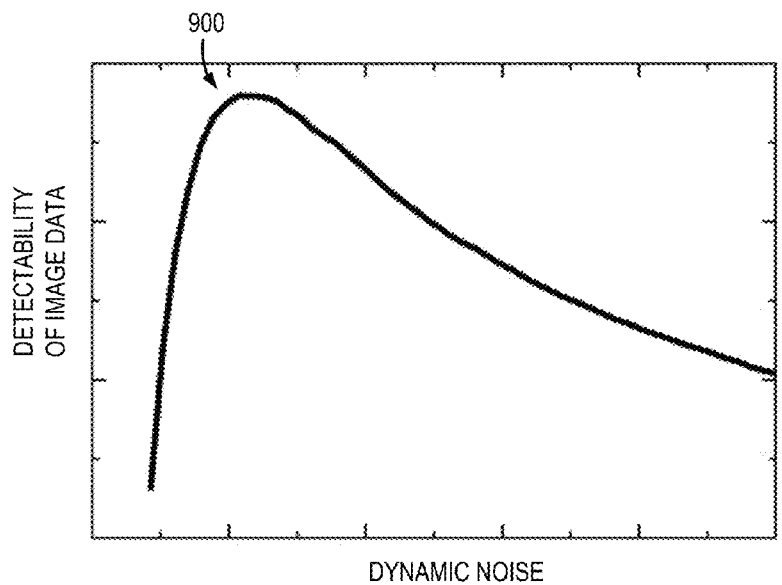
FIG. 9 is a graph showing a general relationship between a level of noise associated with a given level of image data and illustrating that desired levels of dynamic noise can be used to help detection accuracy, while higher and lower levels of noise lead to lower detection accuracies.

The present disclosure recognizes, counterintuitively, that in certain circumstances and, when carefully selected, noise can be used to enhance the detection of sub-threshold stimulus whether by humans or electronic systems. This phenomenon is referred herein to as "stochastic resonance." For example, referring to FIG. 9, there is a point 900 where the inclusion of increased noise reaches a maximum relative to the detectability of the image data, which is a point 900 of maximum stochastic resonance. "Stochastic resonance" has been observed in biological neurons and other systems with nonlinear sensing characteristics—specifically systems which have a detection threshold—, and has been applied to improve detection of electronic signals and tactile stimuli in humans. Stochastic resonance techniques have been proposed for certain image enhancement applications, such as to improve the depiction of ridge patterns in fingerprint images.

Prior attempts to apply stochastic resonance have focused on integrating static noise into images and using an image processing algorithm to threshold the images at a specific intensity level to improve the detection of objects or features in a final static image by a human observer or a processing algorithm. Explicit thresholding of an image is a type of simplistic image enhancement, which may reduce information in the image if the threshold is not well-selected or if the image has inhomogeneous average intensity across different areas (e.g. any MRI image). Thus, the thresholding step can result in obscuring or losing the desired information. Further, since only one image with static noise is generated, it may enhance or, more likely, deteriorate the image.

As will be described, the present disclosure provides systems and methods for the addition of carefully-determined levels of dynamic (time-varying) noise to an image during viewing to enhance detectability of desired objects or features by exploiting stochastic resonance phenomena. That is, as will be described, the present disclosure provides systems and methods for viewing medical images using a display, whereby dynamic noise is introduced to the displayed images to augment visual feature detection in the retina and brain of the observer using the display to view images. To this end, the present disclosure can be used to enhance images by expanding them into a larger series with properties, such as spatial characteristics, intensity, or color of the images varying over time, and even by varying the way in which such modulation or variations are applied to the original images.

Thus, the present disclosure recognizes that, since stochastic resonance does not suppress features in the image and the added noise can have a very broad range of spatial frequencies, it will affect any type of object. Similarly, intensity variation or color variation, in colored images, can span a broad spectrum and affect any type of object that may be present in the images. Thus, knowledge of object/image/native noise properties, while potentially helpful, is not necessary. Dynamic noise spatial frequencies (or e.g. colors) are broad enough to achieve overlap with an object's spatial frequencies; thus, creating "visual detection noise." Because the detection of an object is a binary decision (presence or non-presence), any information with evidence below the detection threshold is discarded. Since dynamic noise can present a low overall level, the false positives from noise alone are not detected. For an object near or below the detection threshold, the overlap of the object with dynamic noise which contains object-like features (e.g. spatial frequencies) within its broad spectrum can bring the object above the detection threshold and enhance its detection. Furthermore, reviewing multiple frames (or cycles of frames) allows the human observer to make use of the frames that have detectability enhanced by the dynamic noise while more easily ignoring the frames that have detectability lowered by the dynamic noise. To this end, as will be described, the present disclosure can directly show the dynamically modified images to the human observer. In this way, the entire human visual object detection system (object identified as present or not) can be used as the detector. An algorithm designed to accurately model the human visual object detection can still be used to detect objects in dynamically modified images. Notably, the detection threshold in the human observer has a probabilistic component as the same person may not always detect an object in the same image or in different images with the same contrast-to-noise. Thus, a difficult-to-detect object below the detection threshold is defined as an object which is relatively unlikely (e.g., statistically, less than, for example, 50% probability of detection) to be detected by a human observer.

As will be described, the systems and methods of the present disclosure may be used with a variety of imaging systems or modalities or images created using any such systems or modalities. Following herein is a description of a few examples of imaging systems that may be used to acquire images that may be modified to enhance detectability using the systems and methods of the present disclosure. To this end, the systems and methods of the present disclosure may be integrated with these or other imaging systems or modalities. However, as will also be described, the systems and methods of the present disclosure may also be utilized apart from the particular systems that acquire medical images. That is, the systems and methods of the present disclosure may be used to enhance medical images that have been previously acquired (even at different times and locations) or pre-processed. Before turning to such stand-alone methods and systems, a brief description is provided of a few examples of the imaging systems or modalities that may produce imaging data for use with the present disclosure or with which the systems and methods of the present disclosure may be integrated. It should be noted that each imaging modality relies upon different mechanisms for contrast and, related thereto, noise. For example, in computed tomography or x-ray, contrast and nose are related to the does of ionizing radiation delivered to the patient. In the case of magnetic resonance, contrast and nose is related to the fidelity of the echo signals that are acquired and, thus, the scan time.

As used herein, an "original image" or "original series of images" may include a low-contrast-to-noise object/set of features that needs to be detected for correct medical diagnosis. "Modified images" or a "modified image" may include a set of images or an image that may include original images modified with several different instances of random noise, such that a modified image refers to an original image modified by changes such as the addition of dynamic or random noise). A "detector" may include a human performing visual review of original or modified images or an algorithm (or combination of device and system) configured to review original or modified images, such that the processing leads to a decision about whether the image/set of images contains an object/features of interest. The features of interest may be a particular pattern (e.g. texture of lung images, identifiable by combinations of edges/intensity patterns, which can be used to diagnose a whole-organ disease).

Figure 1:
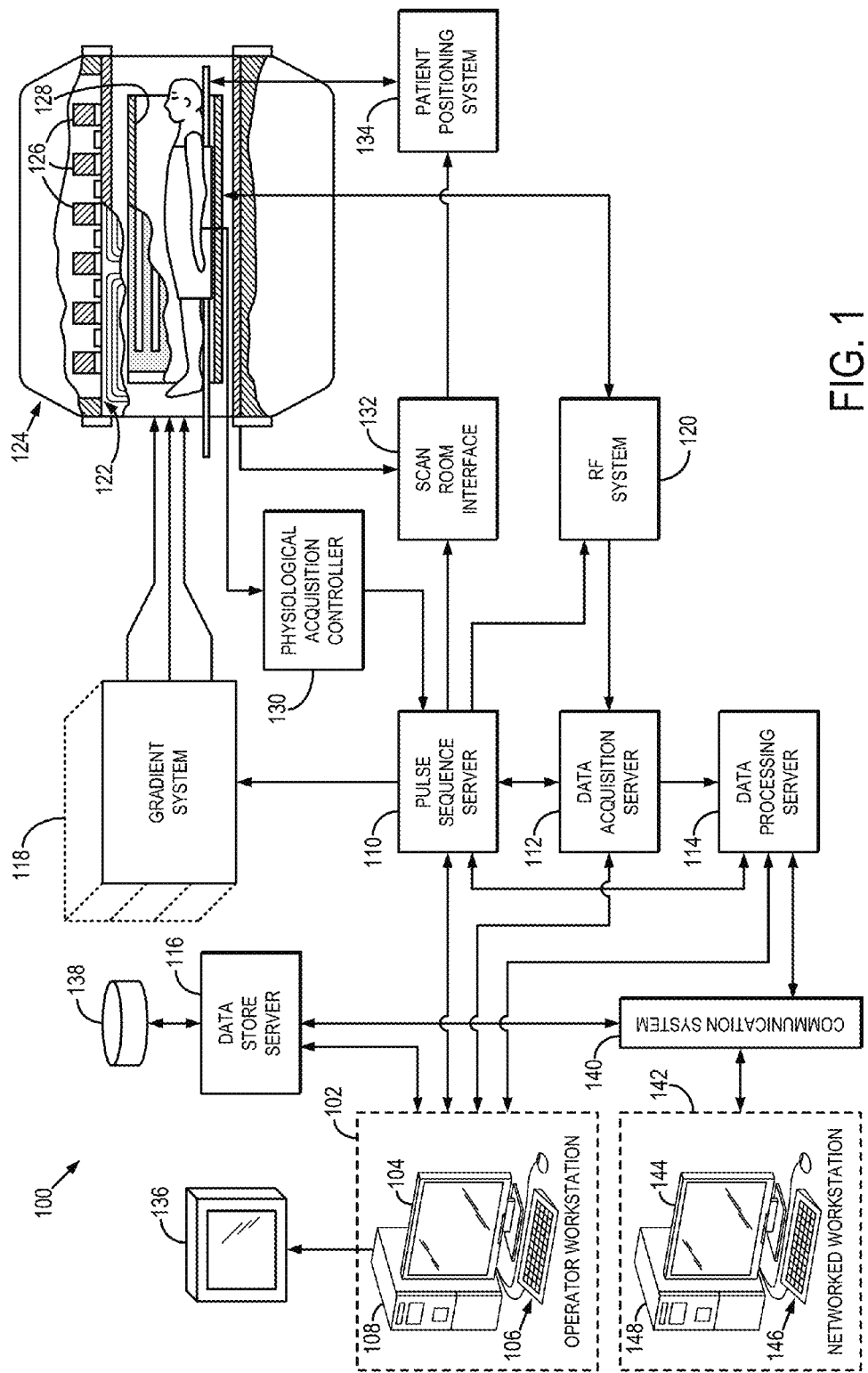
FIG. 1 is a block diagram of an MRI system for use with the present disclosure.

For example, referring to FIG. 1, an example of a magnetic resonance imaging (MRI) system 100 is illustrated. The MRI system 100 includes a workstation 102 having a display 104 and a keyboard 106. The workstation 102 includes a processor 108 that is commercially available to run a commercially-available operating system. The workstation 102 provides the operator interface that enables scan prescriptions to be entered into the MRI system 100. The workstation 102 is coupled to four servers: a pulse sequence server 110; a data acquisition server 112; a data processing server 114; and a data store server 116. The workstation 102 and each server 110, 112, 114, and 116 are connected to communicate with each other.

The pulse sequence server 110 functions in response to instructions downloaded from the workstation 102 to operate a gradient system 118 and a radiofrequency (RF) system 120. Gradient waveforms necessary to perform the prescribed scan are produced and applied to the gradient system 118, which excites gradient coils in an assembly 122 to produce the magnetic field gradients $G_x$, $G_y$, and $G_z$ used for position encoding MR signals. The gradient coil assembly 122 forms part of a magnet assembly 124 that includes a polarizing magnet 126 and a whole-body RF coil 128 (or a head (and neck) RF coil for brain imaging).

RF excitation waveforms are applied to the RF coil 128, or a separate local coil, such as a head coil, by the RF system 120 to perform the prescribed magnetic resonance pulse sequence. Responsive MR signals detected by the RF coil 128, or a separate local coil, are received by the RF system 120, amplified, demodulated, filtered, and digitized under direction of commands produced by the pulse sequence server 110. The RF system 120 includes an RF transmitter for producing a wide variety of RF pulses used in MR pulse sequences. The RF transmitter is responsive to the scan prescription and direction from the pulse sequence server 110 to produce RF pulses of the desired frequency, phase, and pulse amplitude waveform. The generated RF pulses may be applied to the whole body RF coil 128 or to one or more local coils or coil arrays.

The RF system 120 also includes one or more RF receiver channels. Each RF receiver channel includes an RF preamplifier that amplifies the MR signal received by the coil 128 to which it is connected, and a detector that detects and digitizes the quadrature components of the received MR signal. The magnitude of the received MR signal may thus be determined at any sampled point by the square root of the sum of the squares of the I and Q components:

$$M=\sqrt{I^2Q^2} \quad (1);$$

and the phase of the received MR signal may also be determined:

$$\varphi = \tan^{-1}\left(\frac{Q}{I}\right). \quad (2)$$

The pulse sequence server 110 also optionally receives patient data from a physiological acquisition controller 130. The controller 130 receives signals from a number of different sensors connected to the patient, such as electrocardiograph (ECG) signals from electrodes, or respiratory signals from a bellows or other respiratory monitoring device. Such signals are typically used by the pulse sequence server 110 to synchronize, or "gate," the performance of the scan with the subject's heart beat or respiration.

In some instances, the above-described physiological acquisition controller 130 may be specifically adapted to perform magnetic resonance elastography (MRE) studies. Thus, the following systems and methods may be used with MRE processes and MRE images and data. Reference to "MRI" or imaging data, likewise refers to MRE and MRE imaging data.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized MR signal samples produced by the RF system 120 are received by the data acquisition server 112. The data acquisition server 112 operates in response to instructions downloaded from the workstation 102 to receive the real-time MR data and provide buffer storage, such that no data is lost by data overrun. In some scans, the data acquisition server 112 does little more than pass the acquired MR data to the data processor server 114. However, in scans that require information derived from acquired MR data to control the further performance of the scan, the data acquisition server 112 is programmed to produce such information and convey it to the pulse sequence server 110. For example, during prescans, MR data is acquired and used to calibrate the pulse sequence performed by the pulse sequence server 110. Also, navigator signals may be acquired during a scan and used to adjust the operating parameters of the RF system 120 or the gradient system 118, or to control the view order in which k-space is sampled. In all these examples, the data acquisition server 112 acquires MR data and processes it in real-time to produce information that is used to control the scan.

The data processing server 114 receives MR data from the data acquisition server 112 and processes it in accordance with instructions downloaded from the workstation 102. Such processing may include, for example: Fourier transformation of raw k-space MR data to produce two or three-dimensional images; the application of filters to a reconstructed image; the performance of a backprojection image reconstruction of acquired MR data; the generation of functional MR images; and the calculation of motion or flow images.

Images reconstructed by the data processing server 114 are conveyed back to the workstation 102 where they are stored. Real-time images are stored in a data base memory cache (not shown), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the workstation 102. The workstation 102 may be used by an operator to archive the images, produce films, or send the images via a network or communication system 140 to other facilities that may include other networked workstations 142.

The communications system 140 and networked workstation 142 may represent any of the variety of local and remote computer systems that may be included within a given clinical or research facility including the system 100 or other, remote location that can communicate with the system 100. In this regard, the networked workstation 142 may be functionally and capably similar or equivalent to the operator workstation 102, despite being located remotely and communicating over the communication system 140. As such, the networked workstation 142 may have a display 144 and a keyboard 146. The networked workstation 142 includes a processor 148 that is commercially available to run a commercially-available operating system. The networked workstation 142 may be able to provide the operator interface that enables scan prescriptions to be entered into the MRI system 100. Accordingly, as will be further described, in accordance with the present disclosure, images may be displayed and modified using the operator workstation 102 or other networked workstations 142, including PACs systems and the like, and the networked workstations 142 may be remotely located and even include mobile devices and portable workstations.

Figure 2:
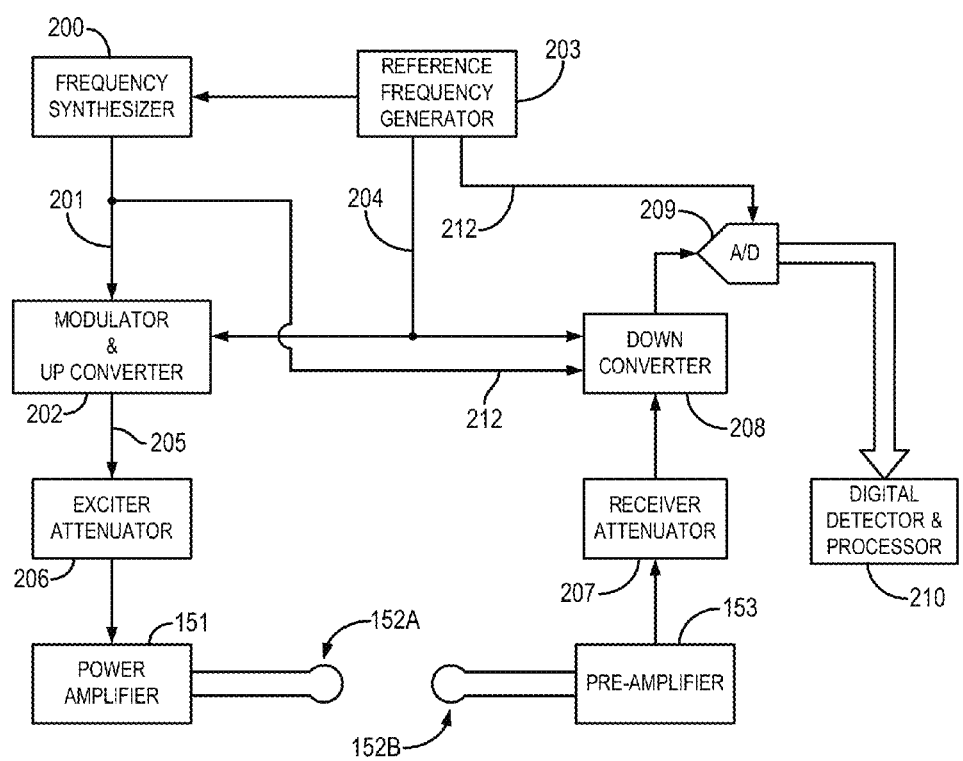
FIG. 2 is a schematic representation of a transceiver system for use with the MRI system of FIG. 1.

As shown in FIG. 1, the RF system 26 may be connected to the whole body RF coil 34, or as shown in FIG. 2, a transmitter section of the RF system 26 may connect to one RF coil 151A and its receiver section may connect to a separate RF receive coil 151B. Often, the transmitter section is connected to the whole body RF coil 34 and each receiver section is connected to a separate local coil 151 B.

Referring particularly to FIG. 2, the RF system 26 includes a transmitter that produces a prescribed RF excitation field. The base, or carrier, frequency of this RF excitation field is produced under control of a frequency synthesizer 200 that receives a set of digital signals from the pulse sequence server 18. These digital signals indicate the frequency and phase of the RF carrier signal produced at an output 201. The RF carrier is applied to a modulator and up converter 202 where its amplitude is modulated in response to a signal R(t) also received from the pulse sequence server 18. The signal R(t) defines the envelope of the RF excitation pulse to be produced and is produced by sequentially reading out a series of stored digital values. These stored digital values may, be changed to enable any desired RF pulse envelope to be produced.

The magnitude of the RF excitation pulse produced at output 205 is attenuated by an exciter attenuator circuit 206 that receives a digital command from the pulse sequence server 18. The attenuated RF excitation pulses are applied to the power amplifier 151 that drives the RF coil 151A.

Referring still to FIG. 2, the signal produced by the subject is received by the receiver coil 152B and applied through a preamplifier 153 to the input of a receiver attenuator 207. The receiver attenuator 207 further amplifies the signal by an amount determined by a digital attenuation signal received from the pulse sequence server 18. The received signal is at or around the Larmor frequency, and this high frequency signal is down converted in a two step process by a down converter 208 that first mixes the NMR signal with the carrier signal on line 201 and then mixes the resulting difference signal with a reference signal on line 204. The down converted NMR signal is applied to the input of an analog-to-digital (A/D) converter 209 that samples and digitizes the analog signal and applies it to a digital detector and signal processor 210 to produce the I values and Q values corresponding to the received signal. As described above, the resulting stream of digitized I and Q values of the received signal are output to the data acquisition server 20 of FIG. 1. The reference signal, as well as the sampling signal applied to the A/D converter 209, is produced by a reference frequency generator 203.

Figure 3A:
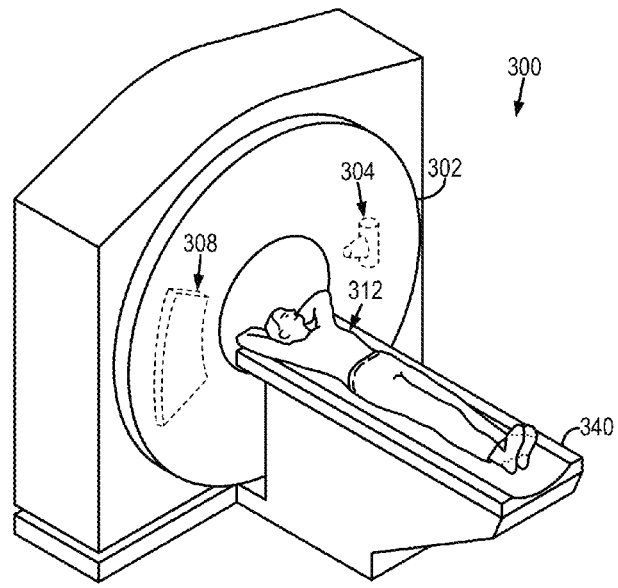
FIG. 3A is a perspective view of a computed tomography (CT) imaging system for use with the present disclosure.
Figure 3B:
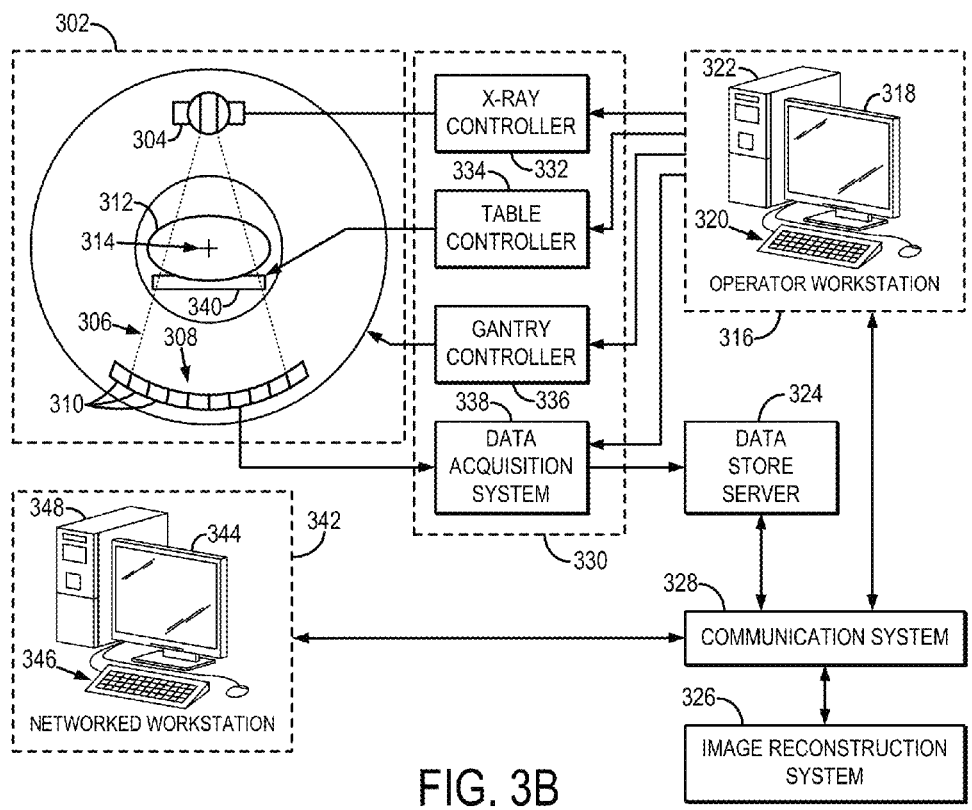
FIG. 3B is a block diagram of the CT imaging system of FIG. 3A.
Figure 4:
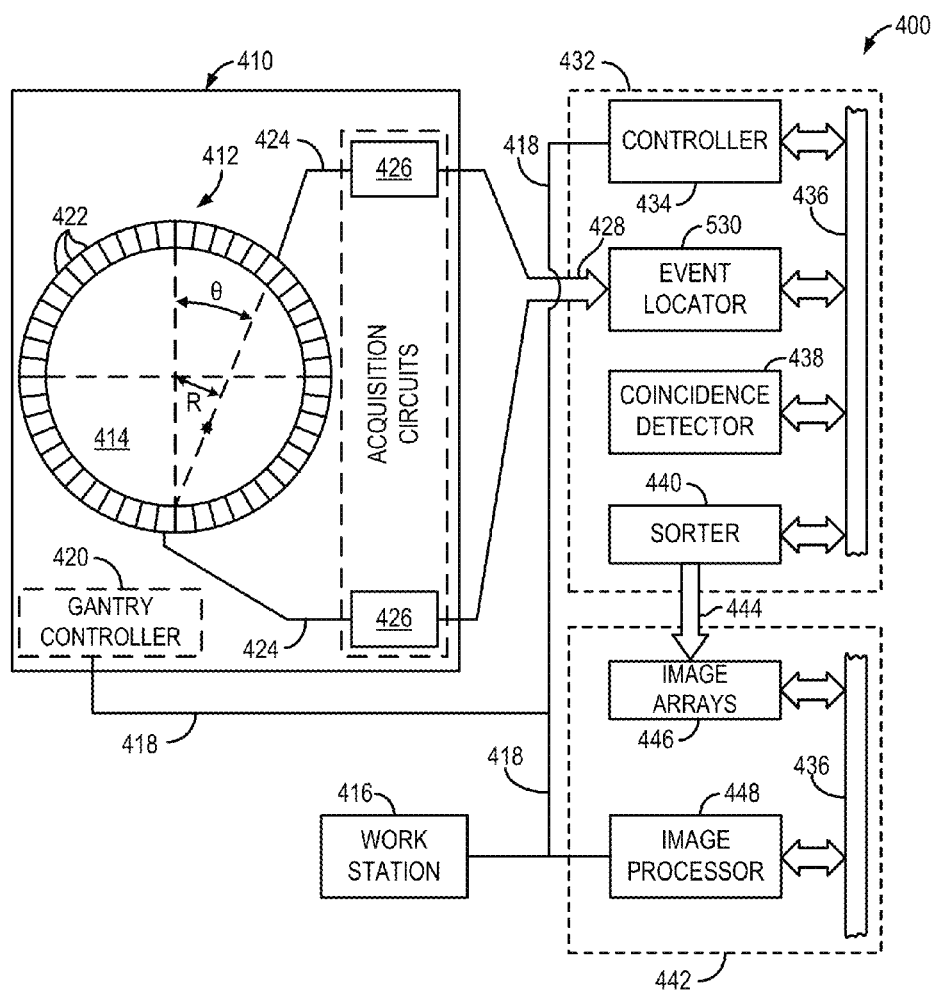
FIG. 4 is a block diagram of a positron emission tomography (PET) imaging system for use with the present disclosure.

Referring now to FIGS. 3A and 3B, an example of an x-ray computed tomography (CT) imaging system 300 is illustrated. The CT system 300 includes a gantry 302, to which at least one x-ray source 304 is coupled. The x-ray source 304 projects an x-ray beam 306, which may be a fan-beam or cone-beam of x-rays, towards a detector array 308 on the opposite side of the gantry 302. The detector array 308 includes a number of x-ray detector elements 310. Together, the x-ray detector elements 310 sense the projected x-rays 306 that pass through a subject 312, such as a medical patient or an object undergoing examination, that is positioned in the CT system 300. As one example, each x-ray detector element 310 produces an electrical signal that may represent the intensity of an impinging x-ray beam and, hence, the attenuation of the beam as it passes through the subject 312. In some configurations, each x-ray detector 310 is capable of counting the number of x-ray photons that impinge upon the detector 310. During a scan to acquire x-ray projection data, the gantry 302 and the components mounted thereon rotate about a center of rotation 314 located within the CT system 300.

The CT system 300 also includes an operator workstation 316, which typically includes a display 318; one or more input devices 320, such as a keyboard and mouse; and a computer processor 322. The computer processor 322 may include a commercially available programmable machine running a commercially available operating system. The operator workstation 316 provides the operator interface that enables scanning control parameters to be entered into the CT system 300. In general, the operator workstation 316 is in communication with a data store server 324 and an image reconstruction system 326. By way of example, the operator workstation 316, data store sever 324, and image reconstruction system 326 may be connected via a communication system 328, which may include any suitable network connection, whether wired, wireless, or a combination of both. As an example, the communication system 328 may include both proprietary or dedicated networks, as well as open networks, such as the internet.

The operator workstation 316 is also in communication with a control system 330 that controls operation of the CT system 300. The control system 330 generally includes an x-ray controller 332, a table controller 334, a gantry controller 336, and a data acquisition system 338. The x-ray controller 332 provides power and timing signals to the x-ray source 304 and the gantry controller 336 controls the rotational speed and position of the gantry 302. The table controller 334 controls a table 340 to position the subject 312 in the gantry 302 of the CT system 300.

The DAS 338 samples data from the detector elements 310 and converts the data to digital signals for subsequent processing. For instance, digitized x-ray data is communicated from the DAS 338 to the data store server 324. The image reconstruction system 326 then retrieves the x-ray data from the data store server 324 and reconstructs an image therefrom. The image reconstruction system 326 may include a commercially available computer processor, or may be a highly parallel computer architecture, such as a system that includes multiple-core processors and massively parallel, high-density computing devices. Optionally, image reconstruction can also be performed on the processor 322 in the operator workstation 316. Reconstructed images can then be communicated back to the data store server 324 for storage or to the operator workstation 316 to be displayed to the operator or clinician.

The CT system 300 may also include one or more networked workstations 342. By way of example, a networked workstation 342 may include a display 344; one or more input devices 346, such as a keyboard and mouse; and a processor 348. The networked workstation 342 may be located within the same facility as the operator workstation 316, or in a different facility, such as a different healthcare institution or clinic.

The networked workstation 342, whether within the same facility or in a different facility as the operator workstation 316, may gain remote access to the data store server 324 and/or the image reconstruction system 326 via the communication system 328. Accordingly, multiple networked workstations 342 may have access to the data store server 324 and/or image reconstruction system 326. In this manner, x-ray data, reconstructed images, or other data may be exchanged between the data store server 324, the image reconstruction system 326, and the networked workstations 342, such that the data or images may be remotely processed by a networked workstation 342. This data may be exchanged in any suitable format, such as in accordance with the transmission control protocol (TCP), the internet protocol (IP), or other known or suitable protocols. Accordingly, as will be further described, in accordance with the present disclosure, images may be displayed and modified using the operator workstation 316 or other networked workstations 342, including PACs systems and the like, and the networked workstations 142 may be remotely located and even include mobile devices and portable workstations.

Figure 5:
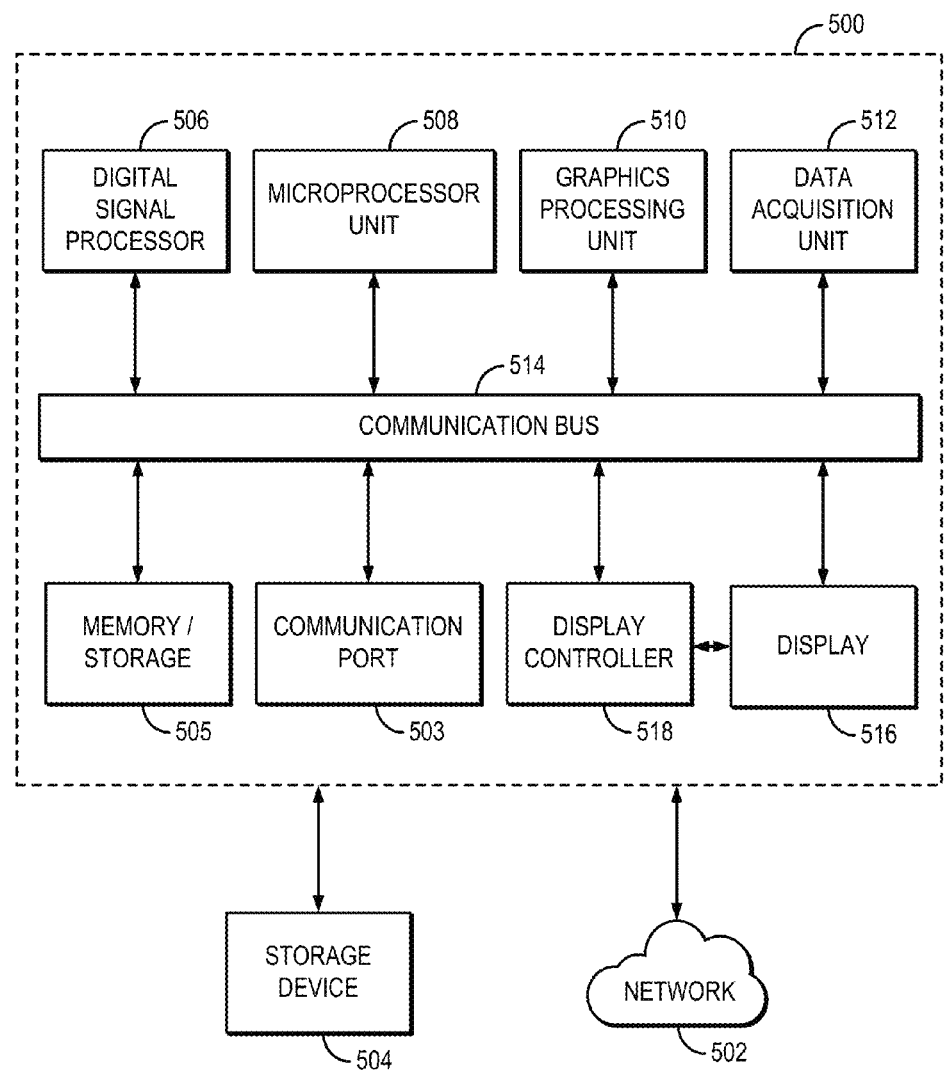
FIG. 5 is a block diagram of an example computer system that can be configured to implement the methods described herein.

Referring now to FIG. 5, a PET system 400 is illustrated that includes a detector system 410 having a detector ring assembly 412. The detector ring assembly 412 is formed of a multitude of radiation detector units 422, represented in this example as block detectors. Each radiation detector unit 422 may include a set of scintillator crystals that is disposed in front of an array of photomultiplier tubes or a position-sensitive photomultiplier tube (not shown), or may be any other suitable radiation detector (for example, such as a high granularity detector). Each radiation detector 422 produces a signal responsive to detection of a photon on communications line 424 when an event occurs. A set of acquisition circuits 426 receive the signals and produce signals indicating the event coordinates (x, y) and the total energy associated with the photons that caused the event. These signals are sent through a cable 428 to an event locator circuit 430. Each acquisition circuit 426 also obtains information from the detector's signals that indicates the exact moment the event took place. For example, with scintillator-type block detectors, digital electronics can obtain this information regarding the precise instant in which the scintillations occurred from the samples of the signals used to obtain energy and event coordinates.

The event locator circuits 430, in some implementations, form part of a data acquisition processing system 432 that processes the signals produced by the acquisition circuits 426. The data acquisition processing system 432 includes a general controller 434 that controls communications, for example, by way of a backplane bus 436 and on the communications network 418. The event locator circuits 430 assemble the information regarding each valid event into a set of numbers that indicate precisely when the event took place, the position in which the event was detected and the energy deposited by the photon. This event data packet is conveyed to a coincidence detector 438 that is also part of the data acquisition processing system 432.

The coincidence detector 438 accepts the event data packets from the event locator circuit 430 and determines if any two of them are in coincidence. The coincidence detector 438 identifies the coincident event pairs located and records them as a coincidence data packet that is provided to a sorter 440. The function of the sorter in many PET imaging systems is to receive the coincidence data packets and generate memory addresses from the coincidence data packets for the efficient storage of the coincidence data. In that context, the set of all projection rays, or lines of response, that point in the same direction (θ) and pass through the scanner's field of view (FOV) is a complete projection, or "view." The distance (R) between a particular line of response and the center of the FOV locates that line of response within the FOV. The sorter 440 counts all of the events that occur on a given line of response (R, θ) during the scan by sorting out the coincidence data packets that indicate an event at the two detectors lying on this line of response.

The sorter 440 provides the image dataset array to an image processing/reconstruction system 442, for example, by way of a communications link 444 to be stored in an image array 446. The image array 446 holds the dataset array for access by an image processor 448 that reconstructs one or more images corresponding to the dataset array. As will be described, images can then be viewed and modified using the work station 416. In manner such as described above, other networked workstations may be used as well, which may be remotely located and even include mobile devices and portable workstations.

Referring now to FIG. 5, a block diagram of an example computer system 500 that can be configured to enhance medical images in accordance with the present disclosure is illustrated. The computer system 500 may be a workstation integrated with any of the above-described medical imaging systems or a variety of other medical imaging systems, including, as non-limiting examples, ultrasound imaging systems, and the like. Furthermore, the computer system 500 may be a workstation integrated within the medical imaging system or may be a separate workstation or mobile device or computing system. To this end, the following description of particular hardware and configurations of the hardware of the example computer system 500 is for illustrative purposes. Some computer systems may have varied, combined, or different hardware configurations.

The medical imaging data acquired by the above-described medical imaging systems or other imaging system can be provided to the computer system 500 from the respective medical imaging systems, such as over a network connection 502, or from a data storage device 504. To this end, the computer system 500 may include a communications port or other input port 503 for communication with the network 502 or the storage device 504. Also, the computer system 500 may include memory and storage capacity 505 to store and access data or images received.

In some configuration, computer system 500 may include one or more processing systems or subsystems. That is, the computer system 500 may include one or more physical or virtual processors. As an example, the computer system 500 may include one or more of a digital signal processor (DSP) 506, a microprocessor unit (MPU) 508, and a graphics processing unit (GPU) 510. If the computer system 500 is integrated into the medical imaging system, a data acquisition unit 512 may be connected directly to the above-described processors 506, 508, 510 over a communications bus 514, instead of communicating acquired data or images via the network 502 or storage device 504. As an example, the communication bus 514 can be a group of wires, or a hardwire used for switching data between the peripherals or between any component, such as the communication buses described above.

The computer system 500 may also include or be connected to a display 516. To this end, the computer system

500 may include a display controller 518. The display 516 may be a monitor connected to the computer system 500 or maybe integrated with the computer system 500, such as in portable computers or mobile devices.

The present disclosure provides systems and methods that can be used to enhance detectability of objects that have a low contrast-to-noise ratio (CNR) and, thus, are hard to detect. The present disclosure uses stochastic noise to create modified images to increase the probability of the human visual system to detect the low-CNR objects or features that are present in the original images, but difficult to detect in the original images.

This approach is particularly applicable to images that are viewed using an electronic display or softcopy. In many fields such as radiology, there has been a major shift from hardcopy viewing to softcopy viewing for image interpretation. This shift introduces new opportunities to enhance human visual perception that until now have received little attention.

Figure 6:
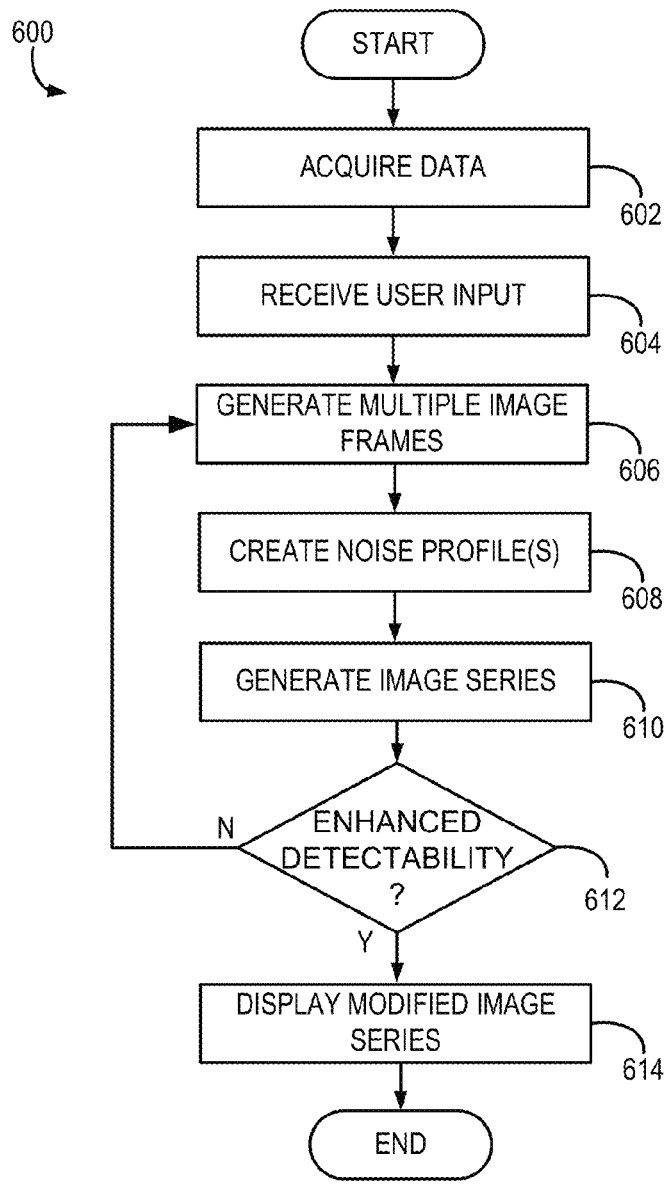
FIG. 6 is a flow chart of steps performed in accordance with one exemplary implementation in accordance with the present disclosure.

Referring now to FIG. 6, a flowchart is provided that includes steps of one non-limiting example that may be performed in accordance with one non-limiting exemplary implementation of the present disclosure. That is, the flowchart of FIG. 6 is only one example that can be used for one setup process for determining desired noise parameters. However, once the parameters are selected or optimized, those parameters can be used across new sets of images without needing to repeat these setup steps. Furthermore, in some settings, desired parameters may be known and, thus, no setup is required. For example, a given manufacturer may generally determine desired noise parameters, for example using the setup process of FIG. 6 or another setup process. In this case, the manufacturer may use such noise parameters across an entire line of products or clinical applications and, thus, the consumer is never subjected to a setup process such as illustrated in FIG. 6. However, optionally, a manufacturer may wish to provide a customer or clinician the ability to select noise parameters that align with personal preferences and, thus, may optionally allow but not require a user to perform a setup process, despite the manufacturer having done an analysis or setup process to identify general noise parameters.

Referring to FIG. 6, at step 602, data are acquired. For example, the user may be at a workstation of a medical imaging system, such as described above, or a stand-along system, or may be using a mobile device to access a set of images. That is, to perform step 602, the user may use a medical imaging system to acquire a set of medical images or may access previously-acquired images. In either case, once the user determines that the medical images could benefit from enhancement, a user provides an indication of a desire to perform an enhancement in accordance with the present disclosure at step 604. This may be done directly from a medical imaging system interface or a workstation integrated with a medical imaging system, or enhancement may be selected from a networked computer or mobile device.

In response to the selection of enhancement at step 604, multiple image frames are generated at step 606. For example, multiple copies of each image or image frame in a series of medical images may be created. Additionally or alternatively, an original image or image set may be stored or a reference to the original image set may be formed before enhancement is performed. At step 608, different instances of dynamic noise, or noise profiles, are generated and are added to the image frames to generate an image series at step 610.

At step 610, the noise added to each of the images or image frames or each of multiple copies of the images or image frames is different. Such noise is referred to herein as "dynamic noise." The dynamic noise can include any of a variety of noise parameters. For example, the noise parameters may vary in the spatial and temporal characteristics and the way in which the noise is added to the original images. For example, the dynamic noise may include noise parameters that may modulate spatial and temporal characteristics of the images. As another example, the dynamic noise may include noise parameters that vary amplitude (intensity) or color of the images. Furthermore, the dynamic noise may include noise parameters that vary the way in which such modulation or variations are applied to the original image or across the multiple instances of the original image.

With dynamic noise added to all frames, some frames of images may become enhanced from the perspective of detecting the object, while others may undergo a neutral or detrimental effect. The frames with objects enhanced and likely detectable by the human visual system can lead to further examination of the surrounding area, while the frames with the object undetectable can be ignored with little detriment. This approach of dynamic noise enhancement is not as practical with the hard-copy medium of the clinical practice in the past, but has broad potential applications when the practice transitions to digital media.

Figure 7:
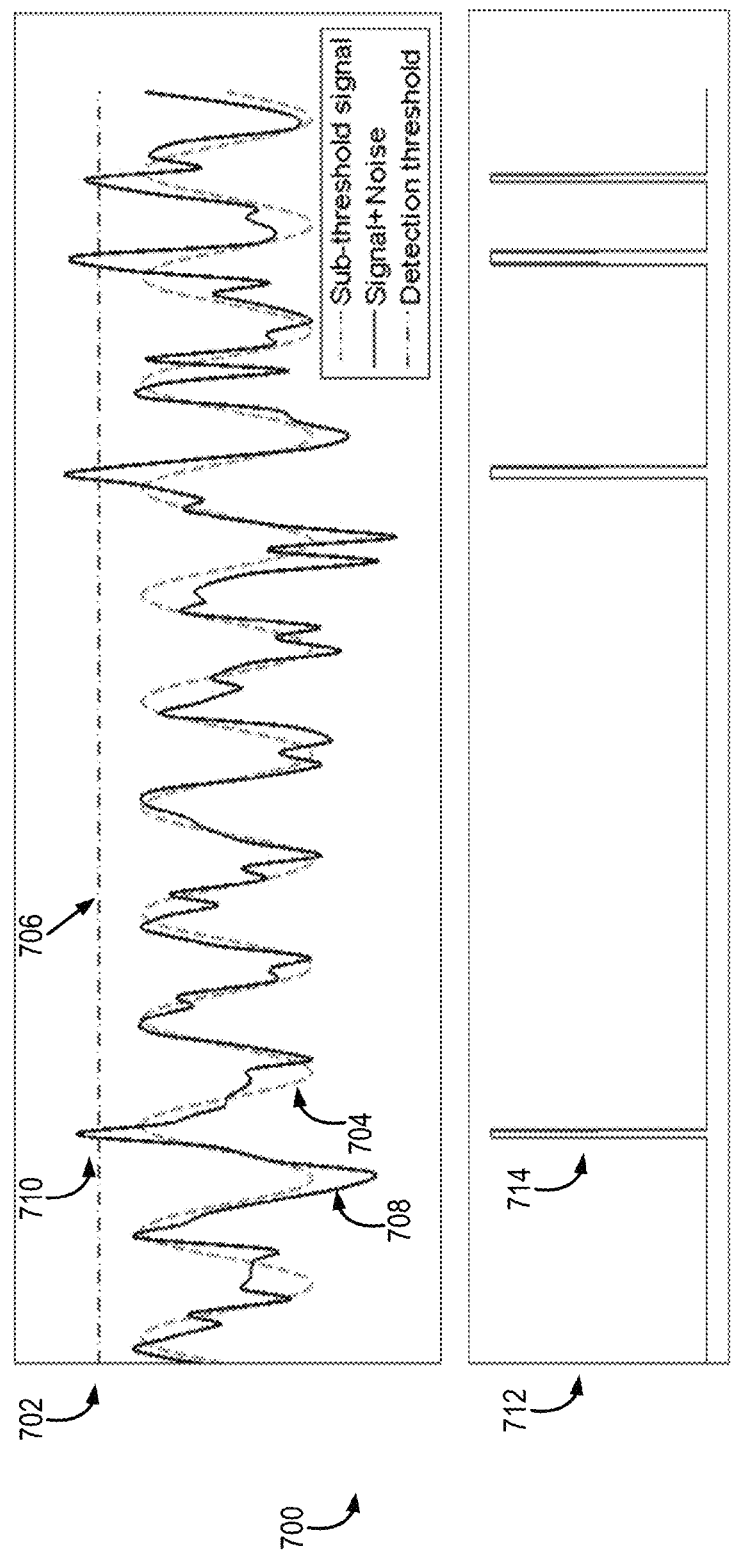
FIG. 7 is a graphic illustration of image signal enhancement techniques in accordance with the present disclosure.

The dynamic noise may be designed to elicit enhancement due to stochastic resonance. Stochastic resonance occurs when a signal that is normally below the threshold of detectability becomes detectable due to the presence of random noise. For example, referring now to FIG. 7, a graphic illustration is provided of stochastic resonance in a graph 700. In a first plot 702, a time-varying signal 704 (the dashed line) is consistently below a given threshold 706 (the dashed-dot line). However, when noise is added to the time-varying signal 704, an enhanced signal 708 (the solid line) is created. With the presence of noise, the original signal 704 sometimes extends above the threshold 706 and becomes detectable, as illustrated, for example, at a given peak 710 of the enhanced signal 708. To this end, a second, correlated, plot 712 shows the detector response of the enhanced signal 708 relative to the threshold 706. The enhanced signal 708 is detectable at peak 701, which corresponds to a discrete peak 714 in the second plot 712. In application to object detection in medical images, as opposed to detection of a one-dimensional signal of varying amplitude, the threshold is defined by the human visual and visual processing systems rather than being a single value. The dynamic noise level that is desirable may be selected by measuring the changes in object detection accuracy by a human observer or by an algorithm that accurately models the physiological visual detection mechanisms.

Referring back to FIG. 6, after generating the image series in step 610, the images are analyzed at decision block 612 to determine if stochastic resonance was achieved with a given set of noise parameters/dynamic noise. In one example implementation, at decision block 612, the image series may be displayed in a loop until user input is received. Enhancement parameters may be varied until improved user accuracy indicative of stochastic resonance is received and verified across multiple enhanced images. As another example, the analysis performed at decision block 612 may be partially or fully automated, such as using an algorithm modeling a human observer, such as described with respect to FIG. 7. Also, the analysis at decision block 612 may include a combination of automated/user analysis and feedback. Regardless of the process for determining favorable noise parameters for the dynamic noise applied to the images, at step 614, an image series modified with the favorable noise parameters can be displayed. As the parameters of this method of image enhancement are much less dependent on the object/image/native noise properties, the optimization of dynamic noise parameters can be independent of imaging modality/detection task. An alternative non-limiting example of the optimization procedure involves displaying multiple sets of images modified with different parameters and having the user select the best parameter range for increasing detectability.

Figure 8:
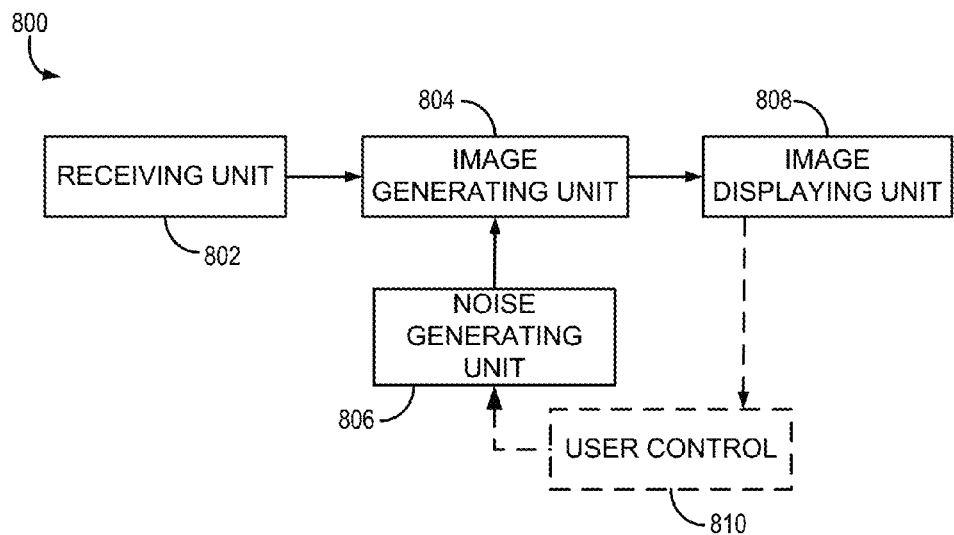
FIG. 8 is a block diagram of a system in accordance with the present disclosure.

Referring now to FIG. 8, a system 800 is provided as an exemplary implementation of a system in accordance with the present disclosure. A receiving unit 802 receives image data. The receiving unit 802 can be a workstation, a terminal in an imaging system, or a mobile device. The receiving unit 802 sends the image data to an image generating unit 804. The image generating unit 804 generates images from the image data added with noise generated by a noise generating unit 806. The noise signal generated by the noise generating unit 806 is dynamic. That is, the noise is generated separately for each enhancing frame and may have constant or variable spatial and temporal characteristics of the modulation, as well as the amplitude, the color, and the way in which the noise is added to the original images. The image generating unit 804 can generate multiple frames of images. One example of the multiple frames of images is duplicates of one single image. As a result, a different noise signal is added to each frame of the single image in the image generating unit 804. The images with added noise are sent to an image displaying unit 808 for display. Optionally, a user may be given access to a user control 810 through which to indicate favorable noise parameters to be used by the noise generating unit 806. The user control is only optional. Thus, in many situations, the user only views the images that are modified with added dynamic noise according to already-determined noise parameters.

EXAMPLE

The above-described systems and methods were tested by measuring the ability of untrained observers to find objects in images with or without enhancement. During the tests, a lesion-screening study was simulated by generating images with a single low-contrast object—a circle with a diameter of 15 pixels—in a 512×512 image with typical medical image noise (referred to as "static noise" here). Human observers were asked to find the location of the object during a 3-second display period. The detectability threshold was defined as a CNR-level at which the probability of finding the object was 50%. For each observer, the CNR was iteratively adjusted until the 50% detection likelihood was reached, i.e. the objects had low enough CNR to be considered sub-threshold.

Two observers evaluated the effectiveness of dynamic stochastic resonance enhancement. Each of them was presented with 300 images, half of which were presented with dynamic noise and half of which were not. The ones with dynamic noise are referred to as "dynamic" and the ones without dynamic noise are referred to as "static" here. The order of images was randomized and the images were not identified as static or dynamic during the viewing. The level of dynamic noise was low and dynamic images were not identifiable during the 3 second display. The level of static noise and the viewing time were the same for all images. The detectability was increased with dynamic noise, as shown below.

TABLE 1

Detectability of images with or without enhancement by dynamic noise.

|            | Static | Dynamic |
|------------|--------|---------|
| Observer 1 | 0.538  | 0.574   |
| Observer 2 | 0.607  | 0.657   |

With the systems and methods described herein, the detectability of the object is noticeably higher. This example tentatively illustrates the effect of stochastic resonance whereby an increased level of noise is associated with increased detection accuracy.

The systems and methods disclosed herein can be applied to enhance any of a variety of types of digital medical images. While separate calibrations for each person may be desirable to determine an optimal or preferred level of dynamic noise to be added, the nature of the object being searched for, or the properties of the imaging modality, do not need to be known as the random noise containing a broad spectrum of spatial frequencies is guaranteed to overlap with the object. So the systems and methods described herein can be used to enhance the sensitivity of low-CNR screening studies where the presence and nature of pathology are not known in advance.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for enhancing the detectability of objects in medical images, the method comprising:
   providing a medical image acquired using a medical imaging system;
   processing the medical image to integrate dynamic noise with the medical image and generate a series of images with varying noise, wherein each image in the series of images with varying noise includes dynamic noise;
   analyzing the series of images with varying noise to determine dynamic noise parameters that achieve an improved detection accuracy; and
   displaying images using the dynamic noise with noise parameters that achieve improved detection accuracy.

2. The method of claim 1 wherein analyzing the series of images includes performing algorithm-based analysis to determine when and under what enhancement parameters stochastic resonance is achieved.

3. The method of claim 1 wherein analyzing the series of images includes receiving a user input indicating an image or series of images with varying noise where the stochastic resonance is achieved.

4. The method of claim 3 further comprising using the user input to identify a dynamic noise with desired noise parameters.

5. The method of claim 4 further comprising applying the dynamic noise with the desired noise parameters to additional medical images associated with the medical image.

6. The method of claim 1 wherein the noise parameters include at least one of modulation of spatial characteristics of the medical image, modulation of temporal characteristics of the medical image, modulation of an amplitude of the medical image, or modulation of color of the medical image.

7. A method for enhancing the detectability of objects in medical images, the method comprising:

providing a medical image acquired using a medical imaging system;
generating, using an image generating unit, multiple instances of the medical image;
integrating dynamic noise signals, generated by a noise generating unit, with each of the multiple instances of the medical image to generate a series of images with varying noise, wherein each of the multiple instances of the medical image is integrated with a different dynamic noise signal to create a series of modified images;
determining dynamic noise parameters that achieve improved detection accuracy; and
displaying, on a display, the series of modified images using the dynamic noise signal parameters that achieve improved detection accuracy.

8. The method of claim 7 wherein the medical image includes a reconstructed image and generating the multiple instances of the medical image includes duplicating the reconstructed image.

9. The method of claim 7 wherein displaying includes cycling through the series of modified images.

10. The method of claim 7 further comprising receiving a user selection of at least one of the series of modified images, or measuring object detection accuracy across the series of modified images.

11. The method of claim 10 further comprising using the user selection of the at least one of the series of modified images, or the user performance across a series of modified images, to identify a desired enhancing noise signal.

12. The method of claim 11 further comprising applying the selected noise signal to additional medical images associated with the medical image.

13. A system for enhancing medical images comprising:
a receiving unit that receives a medical image acquired using a medical imaging system;
an image generating unit that generates multiple instances of the medical image;
a noise generating unit that generates noise signals, wherein the noise signals include dynamic noise with noise parameters that achieve improved detection accuracy;
a noise selection unit that determines dynamic noise parameters that achieve improved detection accuracy;
an image integrating unit that processes the multiple instances of the medical image to integrate the noise signals with each of the multiple instances of the medical image to generate a series of images with varying noise, wherein each image in the series of images with varying noise includes dynamic noise; and
an image displaying unit that displays the series of images using the dynamic noise with noise parameters that achieve improved detection accuracy.

14. The system of claim 13 wherein the medical image is formed by reconstructed images and the multiple instances of the medical image are duplicates of the reconstructed images.

15. The system of claim 13 wherein the imaging displaying unit cycles through the series of images.

16. The system of claim 13 further comprising a user control unit that receives a user selection of at least one of the series of images, or measures user detection accuracy in a set of images with known object positions.

17. The system of claim 16 wherein the noise selection unit identifies parameters of the selected noise signal added to the at least one of the series of images.

18. The system of claim 17 wherein the noise generating unit generates noise signals with parameters similar to those of the selected noise signals and the image integrating unit integrates the selected noise signal to additional medical images associated with the medical image.

* * * * *